(12) United States Patent
Morimoto

(10) Patent No.: US 11,666,489 B2
(45) Date of Patent: *Jun. 6, 2023

(54) WEARABLE ARTICLE HAVING ARTWORK

(71) Applicant: The Procter & Gamble Company, Cincinnati, OH (US)

(72) Inventor: Koichi Morimoto, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 532 days.

This patent is subject to a terminal disclaimer.

(21) Appl. No.: 16/847,707

(22) Filed: Apr. 14, 2020

(65) Prior Publication Data

US 2020/0237569 A1 Jul. 30, 2020

Related U.S. Application Data

(63) Continuation of application No. 15/479,717, filed on Apr. 5, 2017, now Pat. No. 10,660,801, which is a (Continued)

(51) Int. Cl.
*A61F 13/514* (2006.01)
*A61F 13/15* (2006.01)
(Continued)

(52) U.S. Cl.
CPC .. *A61F 13/15203* (2013.01); *A61F 13/49011* (2013.01); *A61F 13/4963* (2013.01); (Continued)

(58) Field of Classification Search
CPC .... A61F 13/49058–49061; A61F 2013/49082; A61F 13/51496; A61F 2013/8497; A61F 2013/15243

See application file for complete search history.

(56) References Cited

U.S. PATENT DOCUMENTS 2,462,195 A 2/1949 Jacobson
2,513,039 A 6/1950 Miller
(Continued)

FOREIGN PATENT DOCUMENTS

CN 2165871 Y 5/1994
CN 2167695 8/1994
(Continued)

OTHER PUBLICATIONS

International Search Report and Written Opinion, PCT/CN2016/078775.
(Continued)

*Primary Examiner* — Susan S Su
(74) *Attorney, Agent, or Firm* — Charles R. Matson

(57) ABSTRACT

Disclosed is a wearable article comprising a main body and a ring-like elastic belt comprising an outer cover layer, a backsheet, a front belt artwork region; and a back belt artwork region; and wherein one or both of the front and back belt artwork regions comprises a belt artwork; a transitional region on the front waist panel and the back waist panel where the outer cover layer exists; and a crotch artwork region on the crotch panel comprising a crotch artwork; wherein at least some of the belt artwork and some of the crotch artwork are printed on the backsheet, wherein when the opacity of the outer cover layer is OC and the opacity of one or both of the front belt and the back belt comprising the belt artwork is OB, respectively, the difference between OC and OB is less than about 20%.

10 Claims, 4 Drawing Sheets

Related U.S. Application Data continuation of application No. PCT/CN2016/078775, filed on Apr. 8, 2016.

(51) Int. Cl.

| | | |
|---|---|---|
| *A61F 13/49* | (2006.01) | |
| *A61F 13/496* | (2006.01) | |
| *A61F 13/505* | (2006.01) | |
| *A61F 13/84* | (2006.01) | |

(52) U.S. Cl.
CPC ...... *A61F 13/505* (2013.01); *A61F 13/51496* (2013.01); *A61F 2013/15243* (2013.01); *A61F 2013/49092* (2013.01); *A61F 2013/8497* (2013.01)

(56) References Cited

U.S. PATENT DOCUMENTS

| | | | |
|---|---|---|---|
| 2,632,177 | A | 3/1953 | Bigger |
| 3,080,869 | A | 3/1963 | Alberts |
| 3,824,812 | A | 7/1974 | Matthews et al. |
| D281,540 | S | 12/1985 | Ternstrom |
| 5,769,838 | A | 6/1998 | Buell et al. |
| 5,787,512 | A | 8/1998 | Knox |
| 7,520,873 | B2 | 4/2009 | Sosalla et al. |
| 7,896,858 | B2 | 3/2011 | Trennepohl et al. |
| 7,901,393 | B2 | 3/2011 | Matsuda et al. |
| 8,282,617 | B2 | 10/2012 | Kaneda |
| 8,377,028 | B2 | 2/2013 | Wheeler |
| 8,518,008 | B2 | 8/2013 | Toshiyasu et al. |
| 8,555,419 | B2 | 10/2013 | Demarest et al. |
| 8,647,319 | B2 | 2/2014 | Een et al. |
| 9,023,006 | B2 | 5/2015 | Shunsuke et al. |
| 9,233,031 | B2 | 1/2016 | Ichihara et al. |
| 9,358,162 | B2 | 6/2016 | Kuwano et al. |
| 9,827,149 | B2 | 11/2017 | LaVon et al. |
| 10,064,763 | B2 | 9/2018 | Takahashi et al. |
| 10,660,801 | B2 | 5/2020 | Morimoto |
| 10,702,424 | B2 | 7/2020 | Morimoto |
| 10,722,408 | B2 | 7/2020 | Morimoto |
| 2004/0243083 | A1 | 12/2004 | Matsuda |
| 2005/0107763 | A1 | 5/2005 | Matsuda et al. |
| 2006/0030831 | A1 | 2/2006 | Matsuda |
| 2007/0032766 | A1 | 2/2007 | Liu et al. |
| 2007/0208317 | A1 | 9/2007 | Krautkramer et al. |
| 2008/0132872 | A1 | 6/2008 | Trennepohl |
| 2010/0298799 | A1 | 11/2010 | Wheeler |
| 2011/0054432 | A1 | 3/2011 | Ueda et al. |
| 2011/0251576 | A1 | 10/2011 | Ando et al. |
| 2012/0226254 | A1 | 9/2012 | Takino |
| 2012/0283682 | A1* | 11/2012 | Otsubo ............ A61F 13/51496 2/400 |
| 2012/0330258 | A1 | 12/2012 | Poruthoor |
| 2013/0079742 | A1 | 3/2013 | Kuwano et al. |
| 2013/0211363 | A1 | 8/2013 | LaVon et al. |
| 2013/0306226 | A1 | 11/2013 | Zink |
| 2013/0310795 | A1 | 11/2013 | Glahn et al. |
| 2013/0310798 | A1 | 11/2013 | Glahn |
| 2013/0317468 | A1* | 11/2013 | Yoshioka .......... A61F 13/49413 604/385.16 |
| 2013/0317471 | A1* | 11/2013 | Morimoto ......... A61F 13/49061 604/385.01 |
| 2014/0163509 | A1* | 6/2014 | Gassner ............ A61F 13/49061 604/385.16 |
| 2014/0228798 | A1 | 8/2014 | Ashton et al. |
| 2014/0288523 | A1 | 9/2014 | Hasse et al. |
| 2014/0358110 | A1 | 12/2014 | Takahashi et al. |
| 2015/0051569 | A1 | 2/2015 | Hashimoto et al. |
| 2016/0058628 | A1 | 3/2016 | Morimoto et al. |

FOREIGN PATENT DOCUMENTS

| | | |
|---|---|---|
| CN | 1246324 | 8/2000 |
| CN | 101180021 A | 5/2008 |
| CN | 101541281 A | 9/2009 |
| CN | 101816600 A | 9/2010 |
| CN | 102596138 A | 7/2012 |
| CN | 103391762 A | 11/2013 |
| CN | 103501741 A | 1/2014 |
| CN | 203436468 U | 2/2014 |
| CN | 105358110 A | 2/2016 |
| EP | 2659870 | 11/2013 |
| JP | H0871107 | 3/1996 |
| JP | H9271488 | 10/1997 |
| JP | 2001212176 | 8/2001 |
| JP | 2007029479 | 2/2007 |
| JP | 2009125087 | 6/2009 |
| JP | 2009160129 A | 7/2009 |
| JP | 2012095937 | 5/2012 |
| JP | 2012135519 | 7/2012 |
| JP | 5566550 | 8/2014 |
| JP | 2014150909 | 8/2014 |
| JP | 2015173751 A | 10/2015 |
| WO | 2008107804 A1 | 9/2008 |
| WO | 2016048337 A1 | 3/2016 |
| WO | WO 2016029655 | 3/2016 |

OTHER PUBLICATIONS

All Office Actions for U.S. Appl. No. 15/479,717.
All Office Actions for U.S. Appl. No. 15/479,672.
All Office Actions for U.S. Appl. No. 15/479,604.
Supplemental ISR and WO, PCT/CN2016/078775.

* cited by examiner

WEARABLE ARTICLE HAVING ARTWORK

CROSS REFERENCE TO RELATED APPLICATION

This application is a continuation of U.S. application Ser. No. 15/479,717, filed on Apr. 5, 2017, which is a continuation of PCT Application No. PCT/CN2016/078775, filed on Apr. 8, 2016, both of which are herein incorporated by reference.

FIELD OF THE INVENTION

The present invention relates to wearable articles having artworks on both the belt artwork region and the crotch artwork region.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult. Absorbent articles are provided with printed artwork to make the article attractive to the wearer and/or the caregiver. Particularly for children, attractive artwork on the article may provide a positive developmental effect. Attractive artwork may be those that connote an undergarment look, are in clear color and shape, or showing characters and objects in noticeable size. Further, attractive artwork may connote high quality to either the wearer or caregiver.

Belt-type pants having a main body to cover the crotch region of the wearer and a separate elastic belt defining the waist opening and leg opening are known in the art, such as described in PCT Publication WO 2008/081930A. Such belt-type pants may be advantageous in that they may have better breathability by having less layers of material in certain areas of the articles, and that they may be manufactured economically. On the other hand, due to the structural difference between the main body, the elastic belt, and the transitional region of the main body and the elastic belt, belt-type pants may be disadvantageous in providing printed artwork that provides an integral appearance.

Based on the foregoing, there is a need for a wearable article with attractive artwork. There is also a need for providing such a wearable article without compromise to the performance as an absorbent article, such as fit, wearability, comfort during wear, prevention of sagging, and prevention of leakage. There is further a need for providing such a wearable article in an economical manner.

SUMMARY OF THE INVENTION

The present invention is directed to a wearable article 20 continuous in a longitudinal direction and a transverse direction comprising a main body 38 and a ring-like elastic belt 40 comprising a front belt 84 and a back belt 86;

the center of the front belt 84 is joined to a front waist panel 52 of the main body 38, the center of the back belt 86 is joined to a back waist panel 54 of the main body 38, the front and back belt each 84, 86 having a left side panel and a right side panel 82 where the main body 38 does not overlap, and the transverse edges 50 of the front belt and the back belt 84, 86 are joined by a seam 32 to form a waist opening and two leg openings; wherein the front belt and back belt 84, 86 are discontinuous of each other;

the main body 38 having a crotch panel 56 between the front waist panel 52 and the back waist panel 54, the main body 38 comprising an outer cover layer 42 at the most garment facing side and a backsheet 60 attached to the body facing surface of the outer cover layer 42; wherein the longitudinal length of the outer cover layer 42 is longer than the longitudinal length of the crotch panel 56 and shorter than the longitudinal length of the backsheet 60;

the wearable article 20 further comprising:

a front belt artwork region 40F disposed on the front waist panel 52 where the outer cover layer 42 is absent; and a back belt artwork region 40B disposed on the back waist panel 54 where the outer cover layer 42 is absent; and wherein one or both of the front belt artwork region 40F and the back belt artwork region 40B comprises a belt artwork 40A;

a transitional region 34F, 34B disposed on the front waist panel 52 and the back waist panel 54 where the outer cover layer 42 is present; and a crotch artwork region 30 disposed on the crotch panel 56 comprising a crotch artwork 40A.

In one aspect of the present invention, at least some of the belt artwork 30A and some of the crotch artwork 40A are printed on the backsheet 60, wherein when the opacity of the outer cover layer is OC and the opacity of one or both of the front belt and the back belt 84, 86 comprising the belt artwork is OB, respectively, the difference between OC and OB is less than about 20%.

In one aspect of the present invention, the belt artwork 40A and the crotch artwork 30A are printed on the backsheet 60, and the belt artwork 40A observed directly on the backsheet 60 is provided in reduced brightness and increased contrast compared to the crotch artwork 30A; such that the intensity of the belt artwork 40A and the crotch artwork 30A appear to be substantially similar when observed as an article from the garment facing side.

In one aspect of the present invention, front belt and the back belt 84, 86 each comprise an inner sheet 94 and an outer sheet 92; wherein the belt artwork 40A is printed on the garment facing surface of the inner sheet 94 or the body facing surface of the outer sheet 92, and the crotch artwork 30A is printed on the backsheet 60.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
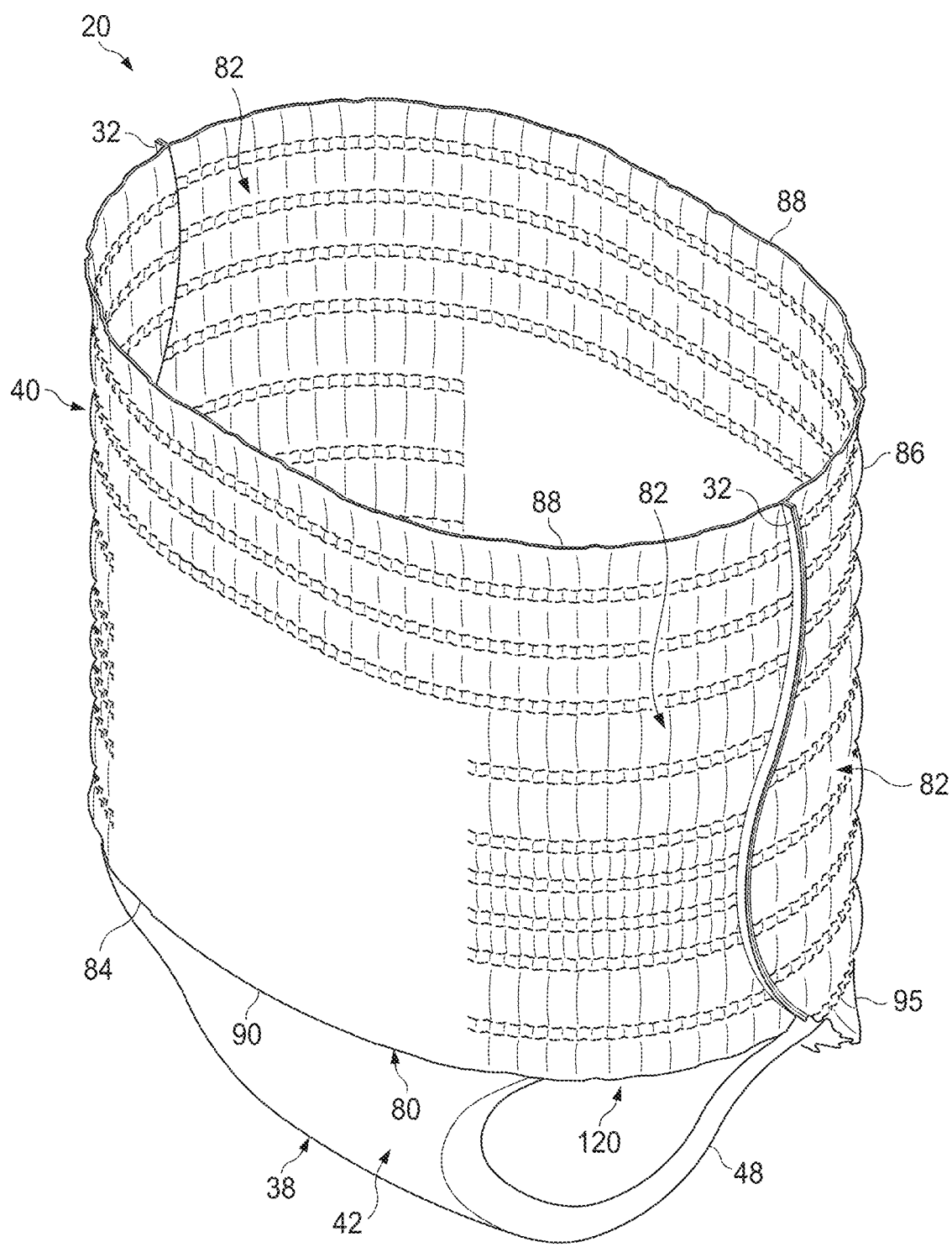
FIG. 1 is a perspective view of one embodiment of a wearable article of the present invention.

As used herein, the following terms shall have the meaning specified thereafter:

"Wearable article" refers to articles of wear which may be in the form of pants, taped diapers, incontinent briefs, feminine hygiene garments, and the like. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having an L* value of at least 94, an a* value equal to 0±2, and a b* value equal to 0±2 according to the "Measurement of Color" described below.

DETAILED DESCRIPTION OF THE INVENTION

Figure 2:
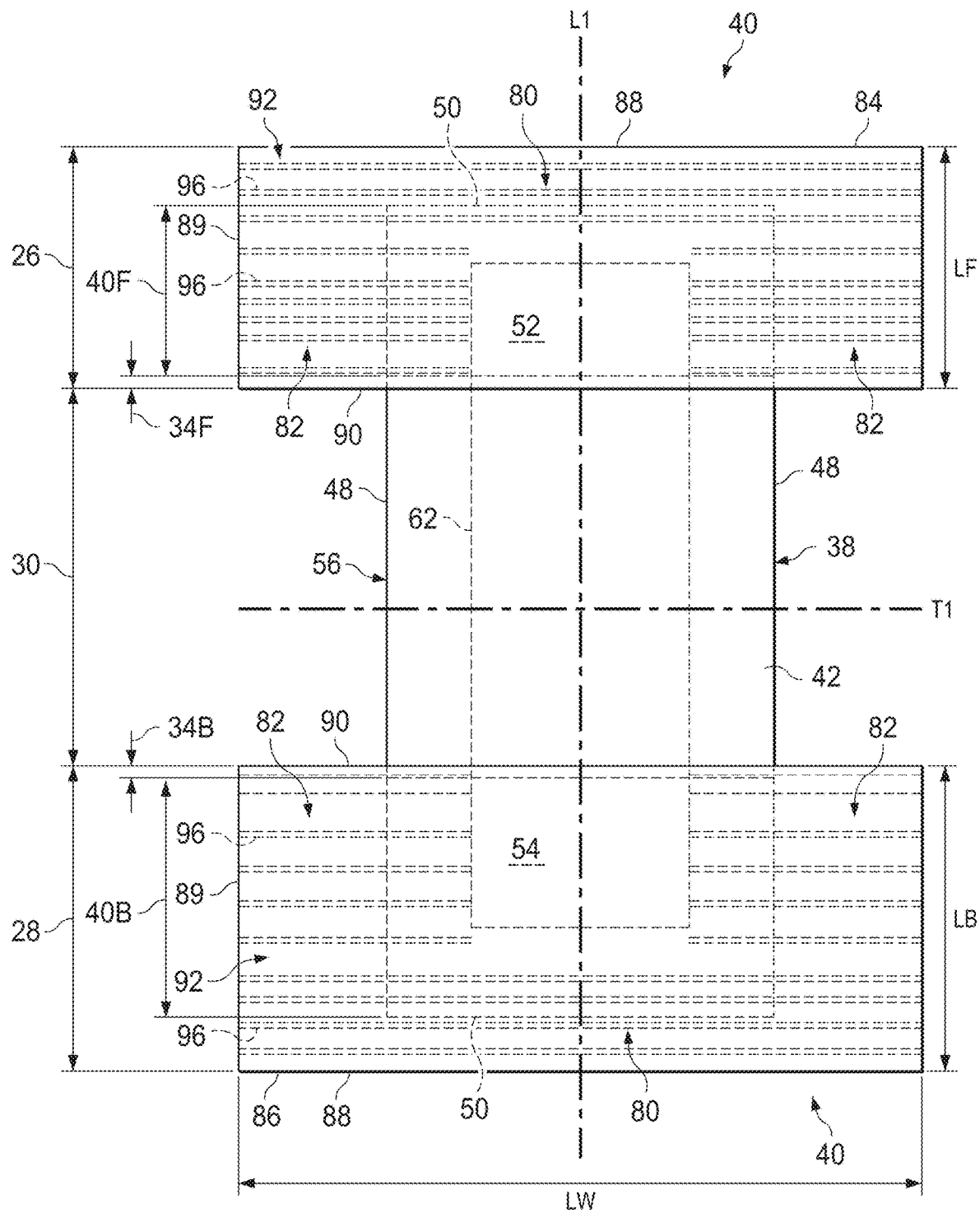
FIG. 2 is a schematic plan view of one embodiment of a wearable article of the present invention with the seams enjoined and in a flat uncontracted condition showing the garment facing surface.

FIG. 1 is a perspective view of an embodiment of the wearable article 20 of the present invention and FIG. 2 is a schematic plan view of the same article with the seams enjoined and in its flat uncontracted condition showing the garment-facing surface. The wearable article 20 has a longitudinal centerline L1 which also serves as the longitudinal axis, and a transverse centerline T1 which also serves as the transverse axis. The wearable article 20 has a body facing surface, a garment facing surface, a front region 26, a back region 28, a crotch (artwork) region 30, and seams 32 which join the front region 26 and the back region 28 to form two leg openings and a waist opening. The wearable article 20 comprises a main body 38 to cover the crotch region of the wearer, a front belt 84 and a back belt 86 (hereinafter may be referred to as "front and back belts"), the front and back belts 84, 86 forming a ring-like elastic belt 40 (hereinafter may be referred to as "waist belt") extending transversely defining the waist opening. The front and back belts 84, 86 and the main body 38 jointly define the leg openings.

Figure 3:
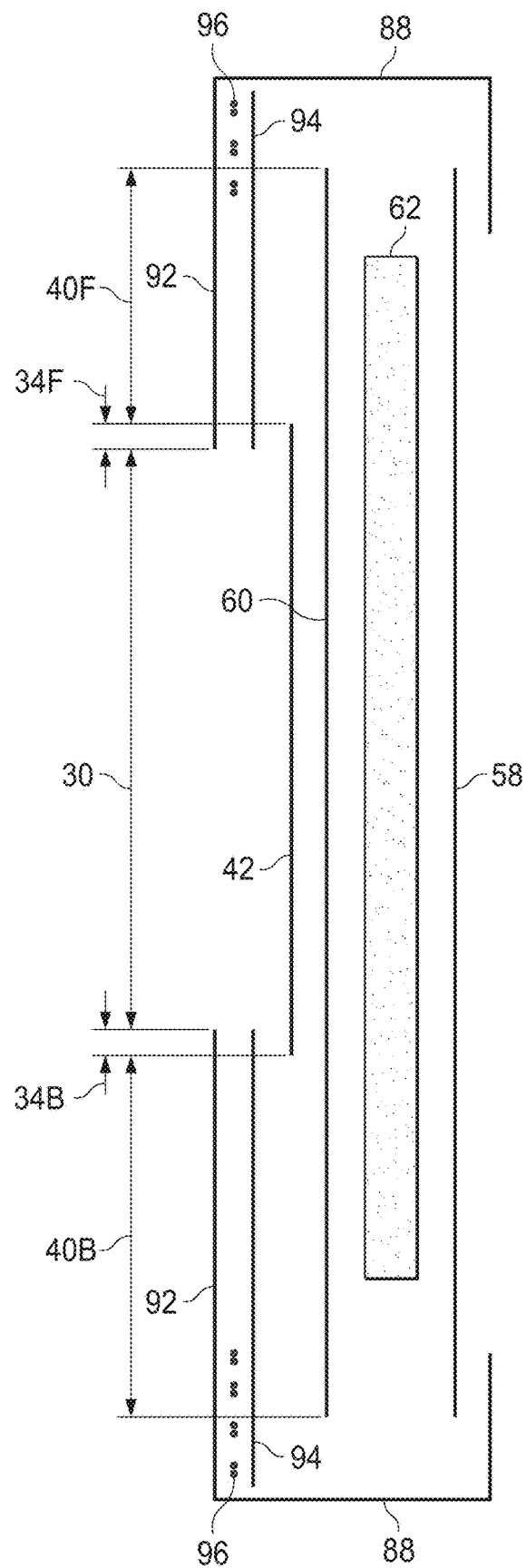
FIG. 3 is a cross section view of FIG. 2 taken along the longitudinal center line.

Referring to FIG. 3, the main body 38 comprises a backsheet 60 and outer cover layer 42 for covering the garment-facing side of the backsheet 60. The backsheet 60 may be a water impermeable film. The outer cover layer 42 may be a nonwoven sheet. The main body 38 may contain an absorbent core 62 for absorbing and containing body exudates disposed on the main body 38. In the embodiment shown in FIG. 2, the main body 38 has a generally rectangular shape, left and right longitudinally extending side edges 48 (hereinafter may be referred to as "side edge") and front and back transversely extending end edges 50 (hereinafter may be referred to as "end edge"). The main body 38 also has a front waist panel 52 positioned in the front region 26 of the wearable article 20, a back waist panel 54 positioned in the back region 28, and a crotch panel 56 between the front and back waist panels 52, 54 in the crotch region 30. The center of the front belt 84 is joined to a front waist panel 52 of the main body 38, the center of the back belt 86 is joined to a back waist panel 54 of the main body 38, the front and back belts 84, 86 each having a left side panel and a right side panel 82 where the main body 38 does not overlap. The main body has a crotch panel 56 positioned between the front waist panel 52 and the back waist panel 54. The front and back belt are discontinuous of each other.

Referring to FIGS. 1 and 2, the ring-like belt 40 formed by the front belt 84 and back belt 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel 56 of the main body 38 than the position of a "distal" portion. Therefore, the proximal edge 90 is located closer than the distal edge 88 relative to the crotch panel 56 of the main body 38. The front and back belts 84, 86 may be joined with each other only at the side edges 89 at the seams 32 to form a wearable article having a waist opening and two leg openings. Each leg opening may be provided with elasticity around the perimeter of the leg opening by the combination of elasticity from the front belt 84, the back belt 86, and any from the main body 38. The front leg opening region 120 is disposed adjacent the leg opening along the proximal edge 90 of the left and right side panels 82 of the front belt 84.

Referring to FIGS. 2 and 3, the front and back belts 84, 86 are discontinuous with one another in the crotch region 30, and therefore the outer cover layer 42 is the garment-facing surface in the crotch region 30. The outer cover layer 42 may extend only partly in the longitudinal direction of the front waist panel 52 and the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, providing better breathability to the overall article, compared to the configuration of FIG. 4. Further, the configuration of FIG. 3, compared to that of FIG. 4, may provide cost saving. Accordingly, looking at the layers of elements between the garment facing surface and the backsheet of the main body 38 of FIG. 3, there are 5 regions from the front distal side to the back distal side; 1) a front belt artwork region 40F disposed on the front waist panel 52 where the outer cover layer 42 is absent; 2) a front transitional region 34F disposed on the front waist panel 52 where the outer cover layer 42 is present; 3) a crotch artwork region 30 disposed on the crotch panel 56; 4) a back transitional region 34B disposed on the back waist panel 54 where the outer cover layer 42 is present; and 5) a back belt artwork region 40B disposed on the back waist panel 54 where the outer cover layer 42 is absent. Hereinafter, the front transitional region 34F and the back transitional region 34B may be collectively referred to as the "transitional region 34F, 34B". The crotch artwork region 30 is made of only the outer cover layer 42 and the belt artwork regions 40F, 40B are made of the layers for making the elastic belt 40, while the transitional region 34F, 34B is made of both the outer cover layer 42 and layers making the elastic belt 40.

The transverse width of the backsheet 60 and the outer cover layer 42 may be the same, or may be varied (not shown). For example, the backsheet 60 may have a shorter transverse width compared to that of the outer cover layer 42. By such configuration, the longitudinal side edges 48 of the crotch panel 56, which make part of the leg openings, may have better breathability. Further, such configuration may provide cost saving.

The front belt 84 and back belt 86 may each comprise an inner sheet 94, an outer sheet 92, (hereinafter also collectively "belt sheets") and configured to impart elasticity to the belt 40. Each of the front and back belts 84, 86 may be made of a single elastic panel, a plurality of elastic panels, or as a laminate having a plurality of belt elastic bodies 96 sandwiched between the inner and outer sheets 94, 92. The belt elastic bodies 96 may extend in the transverse direction to provide a ring like elastic belt 40 when the front belt 84 and the back belt 86 are joined. At least some of the elastic bodies 96 extend in the transverse direction substantially parallel to each other. All of the elastic bodies 96 may extend in the transverse direction substantially parallel to each other. Such an article may be economically made.

The front and back belt 84, 86 may be made of an elastic substrate, or by less than or more than 2 layers. Further, the front belt 84 and the back belt 86 may be made of different materials and/or layers. When the front belt 84 and the back belt 86 are made of the same inner sheet 94, the same outer sheet 92 and plurality of elastic bodies 96 respectively, the elastic bodies 96 may be disposed in the same or different denier, interval, and force between the front and back, as well as in different longitudinal positions of the belt.

The front and/or back belt 84, 86 may be treated such that certain of the area overlapping the front and/or back waist panel 52, 54 of the main body 38 are removed of elasticity. Removal of elasticity from the area where the belt artwork 40A is displayed may help the visibility of the belt artwork 40A. Further, removal of elasticity from certain area of the front and/or back waist panel 52, 54 may be advantageous when the main body 38 comprises an absorbent core 62, in that elasticity in the front and/or back area may cause bunching of the absorbent core 62 and interfere with close fit of the main body 38 to the wearer. In one embodiment, at least a portion of, or at least 10% of, or at least 20% of, or at least 30% of, the elasticity of; at least one of, or at least half of, or at least two thirds of, the elastic bodies are removed in the region overlapping with the front and back waist panels 52, 54 of the main body 38. In one embodiment, the area of all of the elastics 96 overlapping with the belt artwork 40A may be removed of its elasticity.

Referring to FIG. 2, the transverse width LW of the back belt 86 in the uncontracted condition may be the same as the transverse width of the front belt 84 of the same condition. Such an article may be economically made.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams 32 close the front and back belt 84, 86 side edges 89 of the same length for forming the article. Such an article may be economically made.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such configuration, when the wearable article is assembled to form the waist opening and the leg openings, the wearable article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the main body 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

Referring to FIG. 3, the outer sheet 92 of the front or back belt towards the distal edge 88 may be longer than the size of the inner sheet 94 in the longitudinal direction, and an end flap of the outer sheet 92 may be folded over the distal end of the inner sheet 94 at the waist opening to form the waist end region. The front and back belts 84, 86 may be provided in low caliper non-woven material for sake of breathability and softness of the belt 40.

Figure 6:
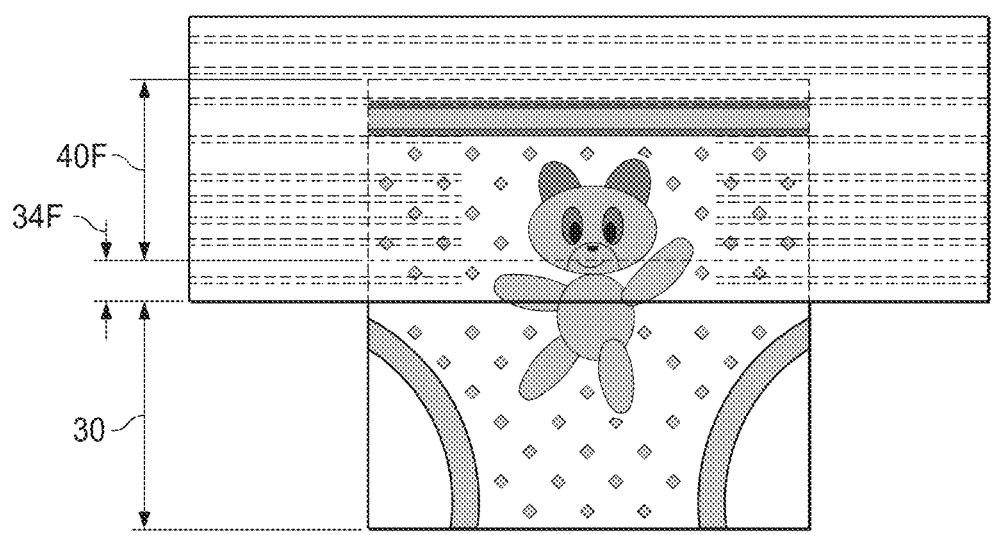
FIG. 6 is a partial schematic plan view of a wearable article.

As explained above, looking at the layers of elements between the garment facing surface and the backsheet of the main body 38, there are 5 regions from the front distal side to the back distal side. When the front and back belt 84, 86 are made of the same inner and outer sheets 94, 92, there are still 3 regions having different layers of elements. For providing attractive printing for a wearable article in an economical manner, it is common practice to provide printing on the garment facing side of the backsheet 60. Referring to FIG. 6, when such printing includes an artwork overlapping more than one region, such as the bear of FIG. 6, the integrity of the artwork is compromised due to the opacity provided by the different number of layers, thereby providing a different appearance to the artwork when observed from the garment facing surface. Such compromised appearance of artwork may connote low quality of the article. The compromised appearance of artwork may be prevented in a number of ways.

The longitudinal length of the transitional region 34F, 34B may be made as short as possible. The longitudinal length of the transitional region 34F, 34B may be less than about 20 mm, or less than about 15 mm, or less than about 10 mm. By providing the transitional region 34F, 34B as short as possible and avoiding displaying artwork in this region, the compromised appearance may be avoided.

It is known that applying of adhesive for joining materials may change the appearance of a material. Namely, adhesives tend to make the substrate to which it is applied more transparent. Adhesive for joining the outer cover layer 42 and the backsheet 60; may have particular impact to artwork disposed on the crotch region 30. As such, the adhesive may at least be applied in the area where the artwork on the crotch region 30 is present. Further, such adhesive may be applied on the entire area of the transitional region 34F, 34B, or the entire area leaving no more than up to 5 mm, in the longitudinal direction, from the distal edge of the transitional region 34F, 34B. The distal edges of the transitional region 34F, 34B matches the distal edges of the outer cover layer 42. By having the adhesive applied on the transitional region 34F, 34B, the opacity of the transitional region 34F, 34B may be decreased. This is particularly advantageous when there is artwork disposed in the transitional region 34F, 34B, as this is the region wherein more layers are present and thus higher in opacity compared to the belt artwork region 40F, 40B, or the crotch artwork region 30. Further, by having the adhesive applied on the transitional region 34F, 34B, wrinkles, fold overs, and other distortions of the outer cover layer 42 may be prevented, thus also preventing increase of opacity in the region.

Figure 5:
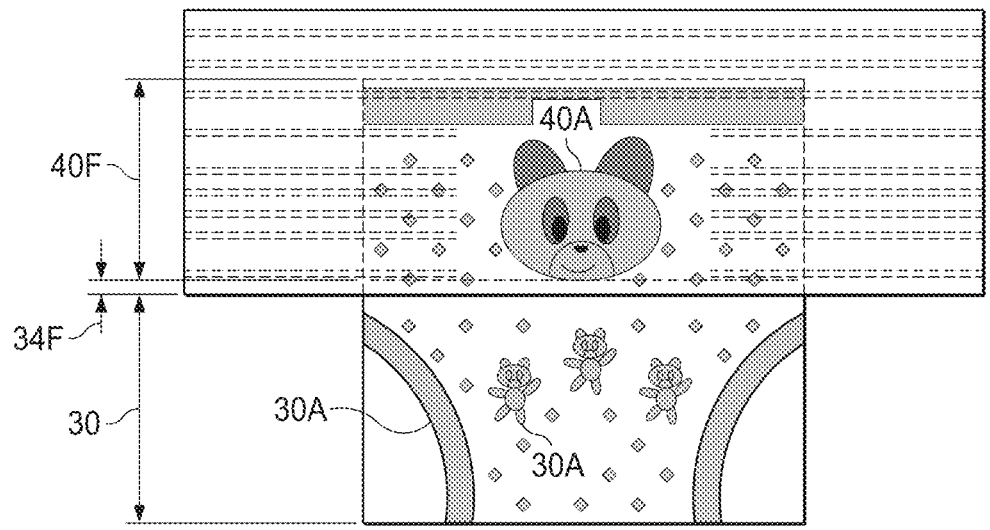
FIG. 5 is a partial schematic plan view of one embodiment of a wearable article of the present invention.

Referring to FIG. 5, in the first present invention, the front and/or back artwork region 34F, 34B may comprise a belt artwork 40A, and the crotch artwork region 30 may comprise a crotch artwork 30A; wherein at least some of the belt artwork 40A and some of the crotch artwork 30A are printed on the backsheet, wherein when the opacity of the outer cover layer 42 is OC and the opacity of one or both of the front belt 84 and the back belt 86 comprising the belt artwork, respectively, is OB, the difference between OC and OB is less than about 20%. The opacity of a sheet material is measured according to the "Measurement of Opacity" described below. By providing OB and OC to have less than about 20% difference, the appearance of the belt artwork 40A and the crotch artwork 30A may be made less different to the observer, and therefore provide visual integrity to the overall artwork of the article. The difference between OC and OB may be less than about 20%, or less than about 15%, or less than about 10%. The value of OC may be from about 15% to about 70%, or from about 20% to about 50%. The value of OB may be from about 15% to about 85%, or from about 20% to about 70%. The values OC and OB may be adjusted by selecting materials for making the belt sheets 92, 94 and the outer cover layer 42, as explained in detail below. All of the belt artwork 40A and the crotch artwork 30A may be printed on the backsheet. The backsheet 60 may be provided with a holistic character as in FIG. 6, collectively by the crotch artwork 30A, artwork provided in the transitional region, and belt artwork 40A. Even when such an artwork is provided, the wearable article 20 of the present invention may maintain visual integrity.

The transitional region 34F, 34B may be free of any artwork (not shown). Alternatively, the transitional region 34F, 34B may have artwork that matches with a transitional or discrete element of the artwork. For example, the neck of an animal, or a transversely extending bar may be disposed on the transitional region 34F, 34B.

Examples of materials suitable for the outer sheet 92 and inner sheet 94 include nonwoven material of 5-50 g/m$^2$. Nonwoven polyolefins such as polypropylene may be suitable for use. Examples of materials suitable for the outer cover layer 42 include nonwoven material of 5-50 g/m$^2$. Patterned, quilted, or embossed material may be useful for connoting softness or high quality of the article.

The outer cover layer 42 may be provided opaque by adding a white-tinting/opacifying agent to the polymer resin that is spun to make the nonwoven material. While a variety of whitening/opacifying agents may suffice, it is believed that titanium dioxide (TiO$_2$) may be particularly effective because of its brightness and relatively high refractive index. It is believed that addition of TiO$_2$ to the polymer(s) from which the fibers are to be formed, typically in an amount up to 5.0% by weight of the nonwoven, may be effective to achieve the desired results. It is believed that the increased opacity provided by whitening/opacifying agents helps to produce a visually distinctive, soft appearance of the nonwoven. It also may be desired in some applications that a coloring or tinting agent be added to one or more the polymer resin(s) from which the nonwoven fibers will be spun.

Opacity can also be enhanced by using fiber having cross-sectional shapes other than round and solid (non-hollow) geometries, namely trilobal or multilobal cross-sections, or hollow configurations or combinations thereof. Those non-circular cross-sectional shapes can also provide advantages in terms of loft and compression resilience.

Spunbonding includes the step of calender-bonding a batt of spunlaid fibers, to consolidate them and bond them together to some extent to create the web as a fabric-like structure and enhance mechanical properties e.g., tensile strength, which may be desirable so the material can sufficiently maintain structural integrity and dimensional stability in subsequent manufacturing processes, and in the final product in use. Calender-bonding may be accomplished by passing the batt through the nip between a pair of rotating calender rollers, thereby compressing and consolidating the fibers to form a nonwoven web. One or both of the rollers may be heated, so as to promote heating, plastic deformation, intermeshing and/or thermal bonding/fusion between superimposed fibers compressed at the nip. The rollers may form operable components of a bonding mechanism in which they are urged together by a controllable amount of force, so as to exert the desired compressing force/pressure at the nip. In some processes an ultrasonic energy source may be included in the bonding mechanism so as to transmit ultrasonic vibration to the fibers, again, to generate heat energy within them and enhance bonding.

One or both of the rollers may have their circumferential surfaces machined, etched, engraved or otherwise formed to have thereon a bonding pattern of bonding protrusions and recessed areas, so that bonding pressure exerted on the batt at the nip is concentrated at the bonding surfaces of the bonding protrusions, and is reduced or substantially eliminated at the recessed areas. The bonding surfaces have bonding surface shapes. As a result, an impressed pattern of bonds between fibers forming the web, having bond impressions and bond shapes corresponding to the pattern and bonding surface shapes of the bonding protrusions on the roller, is formed on the nonwoven web. One roller may have a smooth, unpatterned cylindrical surface so as to constitute an anvil roller, and the other roller may be formed with a pattern as described, to constitute a bonding pattern roller; this combination of rollers will impart a pattern on the web reflecting the pattern on the bonding pattern roller. In some examples both rollers may be formed with patterns, and in particular examples, differing patterns that work in combination to impress a combination pattern on the web such as described in, for example, U.S. Pat. No. 5,370,764.

A repeating pattern of bonding protrusions and recessed areas such as S-shapes, diamond shapes, I-shapes, and V-shapes may be formed onto a bonding roller. The bonding shapes of the bonding protrusions impress like-shaped bond impressions on the web in the calendering process. Repeating patterns of S-shapes and I-shapes may be advantageous in providing visual integrity with the gathers of the front and back belts 84, 86.

The bonding protrusions on a roller will have a height, which may be expressed as a difference between the radius of the roller at the outermost (bonding) surfaces of the bonding protrusions, and the radius of the roller at the recessed areas. The height may be adjusted with the objective of minimizing the amount of material that must be removed from the roller surface by machining or etching to create the desired shapes and pattern, while still providing for sufficient clearance between the roller bearing the bonding protrusions and the opposing roller, at the recessed areas, to accommodate passage of the batt through the nip in areas of the batt not to be bonded (i.e., at the recessed areas), without substantially compressing it, because maximum loft/caliper is the objective. For webs of the type and basis weight contemplated herein, a bonding protrusion height between 0.3 mm and 1.0 mm may be desired, or a bonding protrusion height between 0.5 mm and 0.8 mm, or even a bonding protrusion height between 0.6 mm and 0.7 mm. The bonding surfaces of the bonding protrusions may have an average area between 0.3 mm$^2$ and 10 mm$^2$. The bonding protrusions typically have sides with an angled slope when viewed in cross section through the height thereof.

Nonwoven webs of the type contemplated herein may be calender-bonded at line speed greater than 300 m/min., or 600 m/min., or even 800 m/min., or more, depending upon nonwoven web composition, basis weight, bonding pattern, and equipment and process variables selected. It will be appreciated that at such speeds, the batt and the surfaces of rollers will entrain surrounding air and move it toward the nip. Surface features of a bonding roller as described above, will enhance this effect. It is believed that, as entrained air is carried toward the nip, the decreasing space between the rollers as the nip is approached creates a zone of relatively higher, and increasing, air pressure in front of the nip. A portion of the entrained air under such higher pressure will be urged into and further compressed in the nip, within the recessed areas of the bonding pattern on the roller, and within the interstices of the fibers passing through the nip. It is believed that, as nonwoven web exits the nip, compressed air entrained within the fibers and passing through the nip therewith encounters a zone of relatively lower pressure on the exit side, and accelerates away from the nip in all unobstructed directions as a result. Thus, it is believed that substantial air entrainment, air compression and complex air flows of relatively high velocity occur within and about the batt and web as a result of movement of the batt and rotation of the calender rollers in the calender-bonding process.

It is believed that surface features of a bonding roller including the bonding protrusions affect these air flows. Particularly at the nip, the profiles of bonding protrusions present obstructions to airflow, while the recessed areas between the bonding protrusions present passageways. Thus, it is believed that for certain configurations, shapes, and positions of bonding protrusions, as will be reflected in the bond impressions created in the web, rotational orientation(s) and repeating patterns of the bonding shapes can be selected and formed to have a beneficial effect on these air flows. It is believed, further, that patterns of bonding protrusions having bonding surface shapes with certain features, reflected in the bonding surfaces and the cross sections of the protrusions along planes substantially parallel with the bonding surfaces, rotational orientations relative the plane approximated by the web surface, and spacing, may be employed to channel these air flows in a way that causes them to reposition the fibers during the calender bonding process, such as by teasing or fluffing the fibers, thus providing an enhanced calender-bonded nonwoven web having greater loft/caliper than a similar nonwoven web having other consolidated bond shapes and patterns, all other variables being the same. Other suitable materials for the outer cover layer 42 of the present invention are disclosed in PCT publication WO 2014/047160, herein incorporated by reference.

Referring to FIG. 3, in the second present invention, the belt artwork 40A and the crotch artwork 30A are provided on the backsheet 60, and the belt artwork 40A observed directly on the backsheet 60 is provided in reduced brightness and increased contrast compared to the crotch artwork 30A; such that the intensity of the belt artwork 40A and the crotch artwork 30A appear to be substantially similar when observed as an article from the garment facing side. By providing the artwork in reduced brightness and increased contrast, the artwork is less influenced by opaqueness provided by the overlaying layers of material.

Referring to FIG. 3, in the third present invention, the front belt 84 and the back belt 86 each comprise an inner sheet 94 and an outer sheet 92 wherein the belt artwork 40A is printed on the garment facing surface of the inner sheet 94 or the body facing surface of the outer sheet 92, and the crotch artwork 30A is printed on the backsheet 60. By printing the artwork in these specific layers, the number of layers between the garment facing surface and the printing is made equal, thus the appearance difference may be alleviated. The opacity difference between the outer sheet 92 and the outer cover layer 42 may be less than about 20%, or less than about 15%, or less than about 10%. The outer sheet 92 and the outer cover layer 42 may be the same material. The belt artwork 40A may be printed directly on the inner sheet 94 or the outer sheet 92 by ink, or by disposing a colored web of a predetermined shape.

Measurement of Opacity

The opacity of a material, or material combined, is the degree to which light is blocked by that material. A higher opacity value indicates a higher degree of light block by the material. Opacity may be measured using a 0° illumination/45° detection, circumferential optical geometry, spectrophotometer with a computer interface such as the HunterLab LabScan XE running Universal Software (available from Hunter Associates Laboratory Inc., Reston, Va.). Instrument calibration and measurements are made using the standard white and black calibration plates provided by the vendor. All testing is performed in a room maintained at about 23±2° C. and about 50±5% relative humidity.

The spectrophotometer is configured for the XYZ color scale, D65 illuminant, 10° standard observer, with UV filter set to nominal. The instrument is standardized according to the manufacturer's procedures using the 44.45 mm (1.750 inch) area view. After calibration, the software is set to the Y opacity procedure which prompts the operator to cover the sample with either the white or black calibration tile during the measurement.

To obtain a specimen, lay the sample flat on a bench, body facing surface downward, and 101.6 mm by 101.6 mm portions of sample are cut using scissor for analysis. When the sample is a combined material, they are overlayed to obtain a specimen. Samples are pre-conditioned at 23° C.±2° C. and 50%±5% relative humidity for two hours prior to testing.

Place specimen over the measurement port. The specimen should completely cover the port with the surface corresponding to the garment-facing surface of the article directed toward the port. Cover the specimen with the white standard plate. Take a reading, then remove the white tile and replace it with the black standard tile without moving the specimen. Obtain a second reading, and calculate the opacity as follows:

$$\text{Opacity} = (Y\text{ value}_{(black\ backing)}/Y\text{ Value}_{(white\ backing)}) \times 100$$

A total of three identical material, or materials combined, are analyzed and their opacity results recorded. Calculate and report the average opacity to the nearest 0.1%.

Measurement of Color

The color of the artwork can be measured using the CIE L* a* b* color system (CIELAB). The L*, a*, and b* values are measured from the garment-facing surface of the wearable article 20. As an example, a flat bed scanner capable of scanning a minimum of 24 bit color at 1200 dpi and has manual control of color management (a suitable scanner is an Epson Perfection V750 Pro from Epson America Inc., Long Beach Calif., US, or the like) is used to acquire images. The scanner is calibrated against a color reflection target compliant to ANSI method IT8.7/2-1993 using color management software (a suitable package is MonacoEZColor available from X-Rite Grand Rapids, Mich., US, or the like) to construct a scanner profile. The resulting calibrated scanner profile is opened within an imaging program that supports sampling in CIE L* a* b* (a suitable program is Photoshop S4 available from Adobe Systems Inc., San Jose, Calif., US, or the like) to measure artwork.

Turn on the scanner for 30 minutes prior to calibration. Place the IT8 target face down onto the scanner glass and close the scanner lid. Open the MonacoEZColor software and select acquire image using the Twain software included with the scanner. Within the Twain software deselect the unsharp mask setting and any automatic color correction or color management options that may be included in the software. If the automatic color management cannot be disabled, the scanner is not appropriate for this application. Acquire a preview scan at 200 dpi and 24 bit color. Insure that the scanned image is straight and that the garment-facing surface is facing side-up. Crop the image to the edge of the target, excluding all white space around the target, and acquire the final image. The MonacoEZColor software uses this image to compare with included reference files to create and export a calibrated color profile compatible with Photoshop. After the profile is created the scan resolution (dpi) can be changed, but all other settings must be kept constant while imaging samples.

Identify an area in the garment-facing surface where the artwork of interest is perceived. For convenience of handing, the sample size may be a 75 mm by 75 mm piece, however, as will be appreciated by the person skilled in the art, smaller samples sizes can be used. Keep all layers intact and place all layers on the scanner flat etc. Open the scanner lid and place the specimen onto the scanner glass with the garment-facing surface facing the glass. Cover the specimen with the white background (in this test method white is defined as having L*>94, −2<a*<2, and −2<b*<2) and close the lid. Acquire and import a scan of the specimen into Photoshop at 600 dpi and 24 bit color. Assign the calibrated scanner profile to the image and change the mode to Lab Color ("Lab Color" in Photoshop corresponds to the CIE L* a* b* standard). Select the "eyedropper" color selection tool. Set the sampling size of the tool to include as many pixels as possible within an artwork without including pixels from adjacent non-colored areas. Using the eyedropper tool, measure and record L* a* b* values in the artwork in the nonwoven image.

EXAMPLES

Example 1

Figure 4:
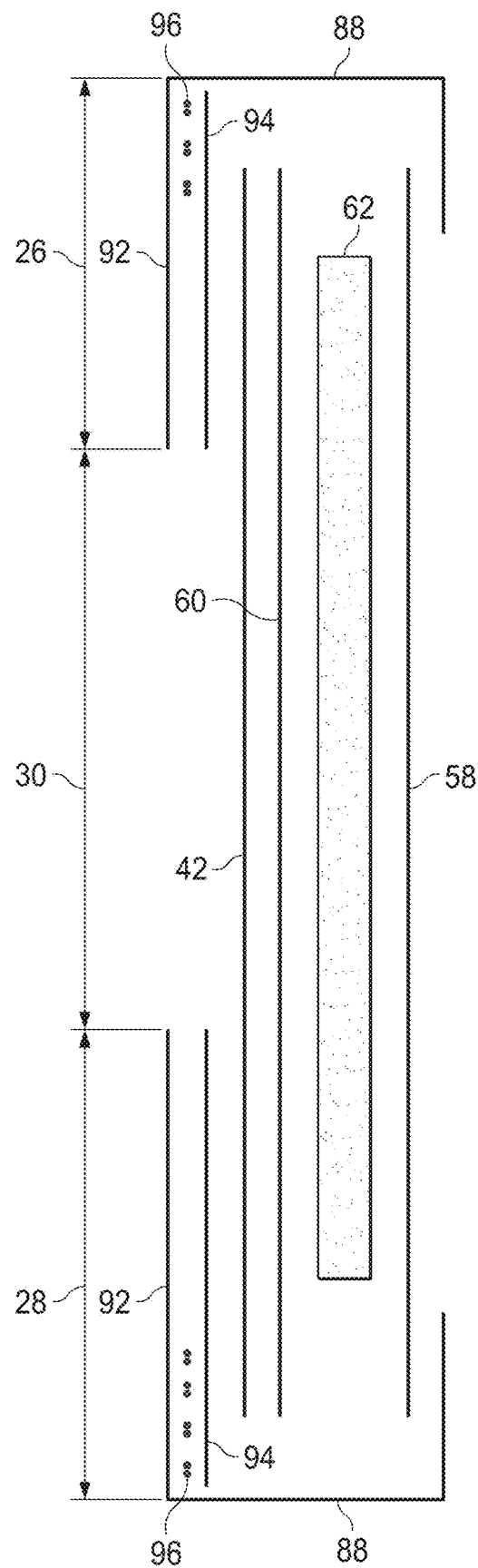
FIG. 4 is a cross section view of a wearable article of the prior art.

Samples A-E having the structure of the belt-type wearable article of FIGS. 2-3, and Samples F-J having the structure of the belt-type wearable article of FIG. 4 are assembled. Samples A-E have a transitional region having a longitudinal length of 10 mm. All samples are provided with the same artwork on the same position of the backsheet 60 having the crotch artwork 30A and belt artwork 40A similar to that of FIG. 5. All Samples have materials for the outer cover layer 42, inner sheet 94, and outer sheet 92, of the same composition, respectively, but in various basis weight ($g/m^2$) according to the Table below.

The OC and OB for each Sample is measured according to the "Measurement of Opacity" herein. The visual integrity of the holistic artwork including the crotch artwork 30A and belt artwork 40A of each Sample is observed by a trained expert panel and evaluated. The results of opacity and the evaluation of "visual integrity" are provided in the Table below.

| Sample | outer cover layer ($g/m^2$) | OC (%) | outer/inner belt sheet ($g/m^2$) | OB (%) | OB – OC (%) | Visual integrity |
|---|---|---|---|---|---|---|
| A | 17 | 20.1 | 17/10 | 37.4 | 17.3 | Good |
| B | 17 | 20.1 | 17/17 | 36.4 | 16.3 | Good |
| C | 25 | 45.4 | 17/10 | 37.4 | −8.0 | Very Good |
| D | 25 | 45.4 | 17/17 | 36.4 | −9.1 | Very Good |
| E | 25 | 45.4 | 25/25 | 70.2 | 24.8 | Bad |
| F | 17 | 20.1 | 17/10 | 50.0(*) | 29.9 | Bad |
| G | 17 | 20.1 | 17/17 | 49.2(*) | 29.1 | Bad |
| H | 25 | 45.4 | 17/10 | 65.9(*) | 20.4 | Fair |
| J | 25 | 45.4 | 17/17 | 65.3(*) | 19.8 | Fair |

(*)For Samples F-J, this value is the opacity provided by the total of the outer cover layer 42 and elastic belt 40 where the belt artwork is displayed.

Inventive Samples A-D of the present invention having an opacity difference of less than 20% provided improved visual integrity of the overall artwork compared to Comparative Samples E-J having an opacity difference of more than about 20%. Inventive Samples A-D are expected to have higher quality perception compared to Comparative Samples E-J.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article, comprising:
    a main body and a ring-like elastic belt comprising a front belt and a back belt; a center of the front belt is joined to a front waist panel of the main body, a center of the back belt is joined to a back waist panel of the main body, the front and back belt each having a left side panel and a right side panel where the main body does not overlap, and the transverse edges of the front belt and the back belt are joined forming a first seam and a second seam to form a waist opening and two leg openings; wherein the front belt and back belt are discontinuous of each other;
    the main body having a crotch panel between the front waist panel and the back waist panel, the main body comprising an outer cover layer at a most garment facing side and a backsheet attached to a body facing surface of the outer cover layer; wherein a longitudinal length of the outer cover layer is longer than a longitudinal length of the crotch panel and shorter than a longitudinal length of the backsheet;
    a front belt artwork region disposed on the front waist panel where the outer cover layer is absent; and a back belt artwork region disposed on the back waist panel where the outer cover layer is absent; and wherein one or both of the front belt artwork region and the back belt artwork region comprises a belt artwork;
    a transitional region disposed on the front waist panel and the back waist panel where the outer cover layer is present; and
    a crotch artwork region disposed on the crotch panel comprising a crotch artwork; wherein at least a portion of the belt artwork and at least a portion of the crotch artwork are printed on the backsheet, wherein when an opacity of the outer cover layer is OC wherein OC is from about 15% to about 70%.

2. The article according to claim 1, wherein an opacity of one or both of the front belt and the back belt comprising the belt artwork is OB, and wherein OB is from about 5% to about 85%.

3. The article according to claim 1, wherein an entirety of the belt artwork and the crotch artwork are printed on the backsheet.

4. The article according to claim 1, wherein the transitional region is free of an artwork.

5. The article according to claim 1, wherein the transitional region comprises a transitional artwork.

6. The article according to claim 1, wherein a longitudinal length of the transitional region is less than about 10 mm.

7. The article according to claim 1, wherein the outer cover layer and the backsheet are joined by an adhesive, wherein the adhesive is at least applied in the area where the crotch artwork is disposed.

8. The article according to claim 7, wherein the adhesive is disposed in an entire area of the transitional region leaving no more than up to about 5 mm, in a longitudinal direction, from a distal edge of the transitional region.

9. The article according to claim 1, wherein the belt artwork is provided in both the front waist panel and the back waist panel, wherein the front belt and the back belt each comprise an inner sheet and an outer sheet, and wherein the front belt and the back belt are made of the same inner sheet material and the same outer sheet material.

10. The article according to claim 1, wherein the backsheet has a shorter transverse width than that of the outer cover layer.

* * * * *